United States Patent
Bruno

[11] 3,970,617
[45] July 20, 1976

[54] NAVY-BLUE NITROPHENYLAZONAPHTHYLAMINO DYES

[75] Inventor: Salvatore A. Bruno, Wilmington, Del.

[73] Assignee: E. I. Du Pont de Nemours and Company, Wilmington, Del.

[22] Filed: Mar. 7, 1974

[21] Appl. No.: 449,064

[52] U.S. Cl. .............................. 260/152; 260/333; 260/345.7; 260/345.9; 260/347.3; 260/347.7; 260/347.8; 260/575
[51] Int. Cl.² ...................... C09B 29/36; D06P 3/54
[58] Field of Search ................................... 260/152

[56] References Cited
UNITED STATES PATENTS

| | | | |
|---|---|---|---|
| 2,135,964 | 11/1938 | Dahlen et al. | 260/166 |
| 2,173,417 | 9/1939 | Huber | 260/198 |
| 2,249,749 | 7/1941 | Dickey et al. | 260/152 |
| 2,266,142 | 12/1941 | Adams | 260/205 |
| 2,373,700 | 4/1945 | McNally et al. | 260/205 |
| 3,598,802 | 8/1971 | Weaver | 260/196 |

FOREIGN PATENTS OR APPLICATIONS

| | | | |
|---|---|---|---|
| 2,116,315 | 10/1971 | Germany | 260/196 |
| 1,320,763 | 6/1973 | United Kingdom | 260/207.1 |
| 1,343,979 | 1/1974 | United Kingdom | 260/196 |

Primary Examiner—Floyd D. Higel
Assistant Examiner—John J. Doll
Attorney, Agent, or Firm—James A. Costello; Earl Christensen

[57] ABSTRACT

Disperse monoazo dyes which are useful for the dyeing and printing of polyester fibers in navy-blue shades and which are of the formula:

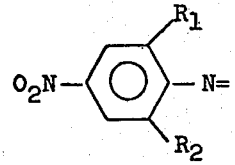

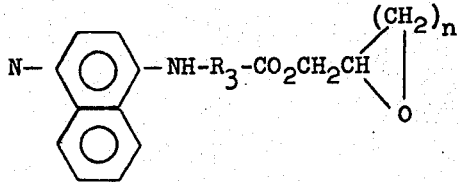

wherein $R_1$ is halogen or CN; $R_2$ is CN or $NO_2$; $R_3$ is alkylene; and $n$ is 3 or 4; said dyes having good light-fastness and good hydrolytic stability.

5 Claims, No Drawings

NAVY-BLUE NITROPHENYLAZONAPHTHYLAMINO DYES

SUMMARY OF THE INVENTION

This invention relates to monoazo disperse dyes which are useful for dyeing and printing polyester fibers in navy-blue shades. There is a great need in the trade for such dyes, especially those having both good light- and sublimation fastness combined with satisfactory application properties, such as buildup and transfer. Currently available navy disperse dyes having satisfactory lightfastness for use on polyester are in many cases deficient in sublimation and/or buildup properties thereon.

It is an object of this invention to provide navy-blue monoazo disperse dyes. It is a further object to provide dyes having good to excellent sublimation and buildup properties. It is a still further object to provide disperse dyes having good light- and dry cleaning fastness, good hydrolytic stability and good transfer properties on polyester fibers. These and other objects are fulfilled by the following invention, wherein the invention has provided a new class of monoazo dyes of the structure:

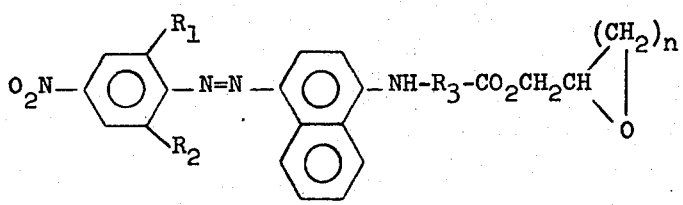

wherein $R_1$ is Br, Cl or CN; $R_2$ is CN or $NO_2$; $R_3$ is $C_{1-4}$ branched or straight-chain alkylene; and $n$ is 3 or 4.

DETAILED DISCUSSION

The monoazo navy dyes of this invention can be prepared by conventional diazotization and coupling procedures wherein a primary aromatic amine of the formula:

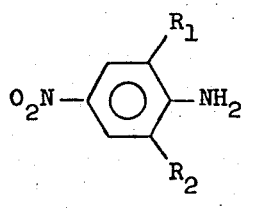

wherein $R_1$ and $R_2$ are as defined above, is diazotized and coupled to an aromatic amine of the formula:

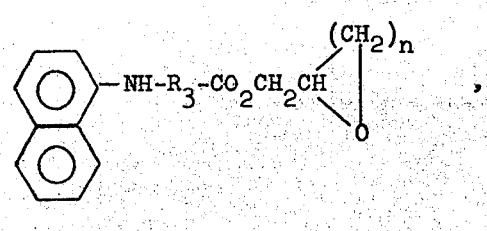

wherein $R_3$ and $n$ are as defined above.

The diazotization of the primary aromatic amine can be carried out at from 0° to 25°C., preferably at 20°–25°C., by the action of nitrosylsulfuric acid in 70–80% aqueous sulfuric acid. Coupling is carried out by dissolving the aromatic amine coupler in an organic or aqueous organic solvent system (such as a mixture of methanol and water), cooling the resultant coupler solution to 15°C. or less and then slowly adding the diazo solution to the cold coupler solution. After the coupling is complete, the disperse dye is precipitated by raising the pH to about 1–3 with a suitable salt or base, such as sodium acetate or sodium hydroxide. The precipitated monoazo dye is isolated by filtration. Examples of diazotizable amines which are useful in the present invention are given in Table I.

TABLE I

Examples of Amines Useful in the Present Invention 2-chloro-4,6-dinitroaniline
2-bromo-4,6-dinitroaniline
2-chloro-6-cyano-4-nitroaniline
2-bromo-6-cyano-4-nitroaniline
2,6-dicyano-4-nitroaniline
2-cyano-4,6-dinitroaniline In order that the invention may be completely understood, the preparation of the coupling components employed in the preparation of the dyes of this invention are given hereinafter. The coupling components can be prepared by methods analogous to those already known in the art. For example, by reaction of an ester of the formula,

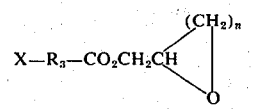

wherein X is Br or Cl and $R_3$ and n are as previously defined, with 1-naphthylamine. Illustrative of such methods are those disclosed in Comptes Rendus, Vol. 145, page 126, and Berichte der Deutschen Chemischen Gesellschaft, Vol. 8, pages 1156 and 1157 (1875).

The aforementioned esters can, in turn, be prepared by reaction of an organic carboxylic acid or chloride with an alcohol of the formula

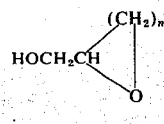

wherein $n$ is as previously defined, according to known procedures. Organic carboxylic acids and chlorides having utility in the subject invention are 2-bromopropionic acid, chloroacetic acid, bromoacetic acid, 3-chloropropionic acid, 4-chlorobutyric acid, 5-chlorovaleric acid, 3-chloropropionyl chloride, 2-bromopropionyl chloride, 4-chlorobutyryl chloride, chloroacetyl chloride and bromoacetyl bromide.

A number of the invention coupling components can also be prepared by the stepwise reaction of 1-naphthylamine with acrylic acid or crotonic acid, followed by esterification of the resulting acid adduct with an alcohol of the formula

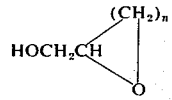

wherein $n$ is as previously defined.

Suitable alcohols include tetrahydrofurfuryl alcohol and tetrahydropyran-2-methanol. Solvents such as toluene and monochlorobenzene can be used in the initial acid condensation reaction in order to obtain reaction mobility and good conversion to the acid adduct. More advantageously, the alcohol to be employed in the esterification process can also be used as solvent in the initial acid condensation reaction. With the alcohol present during the condensation, some esterification occurs and subsequent conversion to coupler can be readily accomplished without any isolation of the intermediate acid adduct. A 2–3 fold molar excess of alcohol to 1-naphthylamine is necessary to insure maximum ester formation in the second step. A 2-fold excess is preferred for economic reasons. Temperatures of from 80° to 100°C. and reaction times from 10 to 25 hours are required to insure essentially complete conversion to acid adduct. A temperature of 90°–95°C. and reaction time of 15 to 17 hours are preferred using the aforementioned preferred molar ratio of reactants.

Upon completion of the acid condensation reaction, both an acid catalyst and, in some cases, a cosolvent are added to facilitate the subsequent esterification process. Catalysts such as sulfuric acid and p-toluenesulfonic acid are both useful in the process. The presence of a cosolvent, such as toluene, allows for the rapid and efficient removal of the water formed in the ensuing esterification. Distillation of the toluene-water azeotrope at from 85° to 120°C. drives the esterification reaction to completion. Removal of the cosolvent by steam distillation, followed by separation of the lower organic product phase from the upper aqueous phase provides the final coupling product in good yield and quality.

Examples of coupling components having utility in the present invention are given in Table II.

Table II

Examples of Coupling Components Useful in the Present Invention

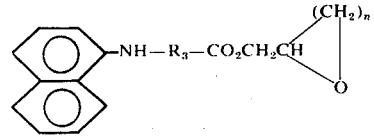

| $R_3$ | n |
|---|---|
| —$C_2H_4$— | 3 |
| —$C_2H_4$— | 4 |
| —CH(CH$_3$)CH$_2$— | 3 |

Table II-continued

Examples of Coupling Components Useful in the Present Invention

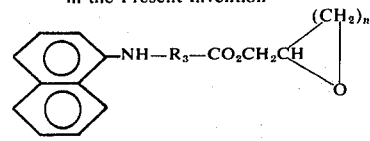

| $R_3$ | n |
|---|---|
| —CH(CH$_3$)CH$_2$— | 4 |
| —(CH$_2$)$_4$— | 3 |
| —CH$_2$— | 3 |
| —(CH$_2$)$_3$— | 4 |
| —CH(CH$_3$)— | 3 |
| —CH$_2$— | 4 |

The crude dyestuffs are conveniently converted into a commercially usable form by mixing the crude dye (e.g. ten parts on a 100% basis) with about 2.5 parts of a lignin sulfonate dispersant and water in a colloid or sandmill. Milling is continued until a fine, stable, aqueous dispersion or paste is obtained with dye particle size reduced to approximately one micron.

The invention dyestuffs have excellent affinity and buildup properties on polyester textile materials, thus enabling deep navy-blue shades to be obtained. The resulting colorations generally have good fastness to light, to wet treatments and in particular to dry heat treatments such as those carried out at high temperature during pleating operations. Surprisingly, analogous prior art dyes of similar molecular weight carrying noncyclic alkyl ether tails are deficient in sublimation fastness and/or buildup properties on polyester.

The invention dyes can be applied to polyester fiber by an aqueous procedure, preferably under pressure, or by padding polyester fibers with an aqueous dispersion of said dyes followed by dry heat (e.g. Thermosol) fixation. Both dyeing procedures are widely used in the trade. The present invention also encompasses polyester fibers dyed or printed with an invention dye. In the Examples which follow, Examples 8 and 9 illustrate the aforementioned aqueous and Thermosol dyeing procedures. Throughout the Examples all parts are given by weight.

EXAMPLE 1 a. A coupling component for the preferred dye of this invention was prepared as follows: A mixture of 30 parts of 1-naphthylamine and 43 parts of tetrahydrofurfuryl alcohol was heated to 80°C. Glacial acrylic acid (16.5 parts) was then added dropwise over a 10 minute period at 80°–85°C. When the addition was complete, the mixture was heated to 90°–95°C. and held at that temperature for 17 hours. The reaction mixture was cooled to 30°C. p-Toluenesulfonic acid (12.5 parts) and toluene (40 parts) were then added and the mixture heated to 85°–95°C. to remove the toluene-water azeotrope. The mixture was cooled to 25°C., washed first with 10% aqueous sodium bicarbonate in order to remove the acidic catalyst, and then with water. The mixture was then heated with steam, distillation of the toluene-water azeotrope commencing at 85°C. The temperature gradually increased during the distillation until at 115°C., almost no distillate was apparent. The mixture was cooled to 85°C. and the lower organic layer was separated to yield 60.5 parts (73% yield) of tetrahydrofurfuryl-3-(1-naphthylamino)propionate having a purity of 76% when analyzed by vapor phase chromatography.

b. 2-Chloro-4,6-dinitroaniline (32.5 parts) was diazotized by adding it in several portions to a stirred solution of 50.2 parts of nitrosylsulfuric acid (38% active ingredient) and 90 parts of 73% sulfuric acid at 20°–25°C. The mixture was stirred at 20°–25°C. for an additional 3 hours. Excess nitrosylsulfuric acid was destroyed with urea.

To synthesize the desired dyestuff the diazo solution was then added dropwise to a cold (0° ± 5°C.) solution of 59 parts of tetrahydrofurfuryl-3-(1-naphthylamino)-propionate (76% purity) from a) above in 750 parts of 70% aqueous methanol. The resulting reddish-brown slurry was stirred at 0° ± 5°C. for 0.5 hour. The pH of the dye mixture was adjusted to approximately 2 by the dropwise addition of 120 parts of 30% aqueous sodium hydroxide. The precipitated dye was collected by filtration, washed acid-free with water and dried to give 69.7 parts (88% yield) of product. Recrystallization from isopropanol-dimethylformamide provided an analytically pure sample, m.p. 166°–168°C., having an absorptivity ($a_{max}$) of 73 liters g.$^{-1}$cm.$^{-1}$ at a wavelength ($\lambda_{max}$) of 606 m$\mu$. The dye was of this formula:

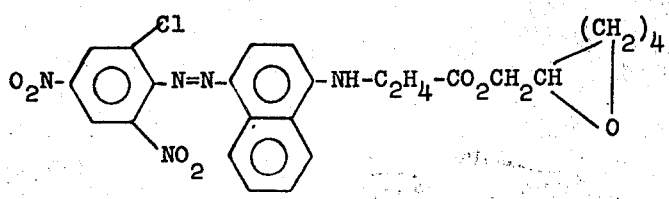

EXAMPLE 2

The procedure of Example 1, part (a) above was repeated except that the tetrahydrofurfuryl alcohol was replaced by 48.7 parts of tetrahydropyran-2-methanol. 2-Chloro-4,6-dinitroaniline was diazotized as described in Example 1, part (b) and coupled to the aforementioned coupling component providing a monoazo dye, m.p. 177°–181°C., having an absorptivity ($a_{max}$) of 71 liters g.$^{-1}$cm.$^{-1}$ at a wavelength ($\lambda_{max}$) of 607 m$\mu$. The dye was of this formula:

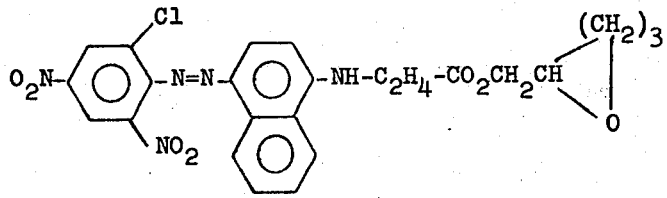

EXAMPLES 3–7

The dyes shown in Table III were prepared by procedures similar to those described in Examples 1 and 2. The R groups and n have the same significance as in the aforesaid formula.

Table III

| No. | $R_1$ | $R_2$ | $R_3$ | n | $\lambda_{max}$ (m$\mu$) | $a_{max}$ (l.g.$^{-1}$cm.$^{-1}$) |
|---|---|---|---|---|---|---|
| 3 | Br | NO$_2$ | —C$_2$H$_4$— | 3 | 608 | 63 |
| 4 | Br | CN | —C$_2$H$_4$— | 3 | 618 | 69 |
| 5 | Cl | CN | —C$_2$H$_4$— | 3 | 621 | 76 |
| 6 | CN | CN | —C$_2$H$_4$— | 3 | 660 | 99 |
| 7 | CN | NO$_2$ | —C$_2$H$_4$— | 3 | 642 | 91 |

EXAMPLE 8 — AQUEOUS (PRESSURE) DYEING PROCEDURE

Five grams of commercially available Dacron 54 polyester fabric were put into an autoclave containing: an aqueous dye paste (15% active ingredient) containing

| | |
|---|---|
| the dye of Example 1 | 0.1 gram |
| "Avitone" T sodium hydrocarbon sulfonate (10% solution) | 1.0 ml. |
| "Merpol" HCS long-chain alcohol-ethylene oxide adduct (10% solution) | 0.5 ml. |
| ethylenediaminetetraacetic acid, sodium salt (1% solution) | 1.25 ml. |
| butyl benzoate carrier (10% emulsion) | 1.5 ml. |
| water | to 75 ml. |
| acetic acid | to adjust the pH to 5.5. |

The temperature was raised to 265°F. for 1 hour to effect dyeing. The dyed fabric was rinsed in water and then dried. It exhibited a navy shade of good fastness to light and excellent fastness to sublimation.

EXAMPLE 9 — THERMOSOL PROCEDURE

Dacron polyester fabric was immersed for 15 minutes at 82°C. in an aqueous bath containing 1% of a commercially available ether-alcohol sulfate surface-active agent (detergent) and 1% of tetrasodium pyrophosphate. The fabric was rinsed in cold water, dried and then padded at 50–60% pickup, based on the dry fabric weight, in a dye bath containing:

| | |
|---|---|
| an aqueous dye paste (15% active ingredient) containing the dye of Example 2 | 50 grams |
| purified natural gum thickener | 20 grams |
| water | to 1 liter. |

The padded material was passed through an infrared predryer, then heated to and held at 213°C. for 90 seconds. The fabric was rinsed in water at 27°C., scoured for 5 minutes at 93°C. in water containing 1% of a commercially available ether-alcohol sulfate detergent, rinsed in water at 27°C. and dried. The polyester fabric was dyed to an attractive navy shade having excellent fastness to sublimation.

What is claimed is:

1. Disperse monoazo dye of the formula:

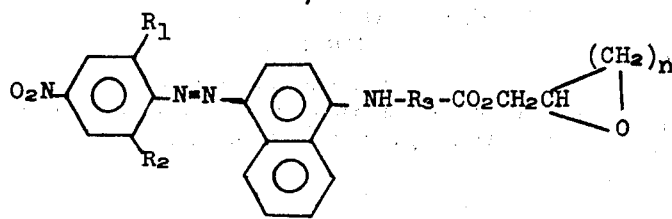
wherein $R_1$ is Br, Cl or CN; $R_2$ is CN or $NO_2$; $R_3$ is $C_{1-4}$ branched or straight-chain alkylene; and $n$ is 3 or 4.
2. The dye of claim 1 wherein $R_1$ is Br or Cl.
3. A dye of claim 1 having the formula:
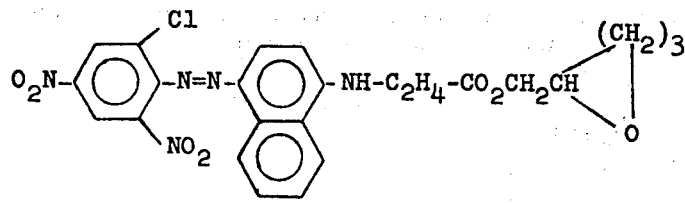
4. A dye of claim 1 having the formula:
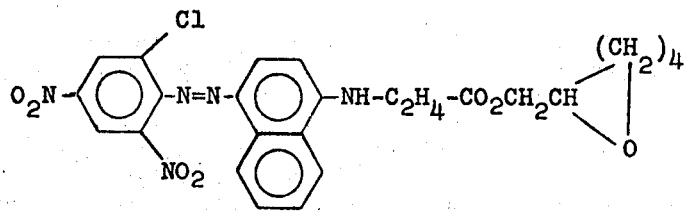
5. A dye of claim 1 having the formula:
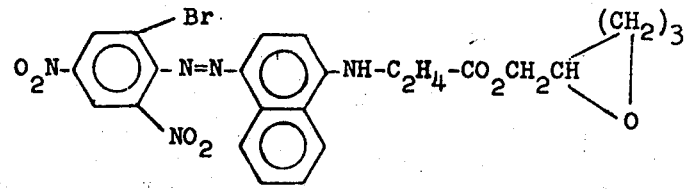
* * * * *

UNITED STATES PATENT OFFICE
CERTIFICATE OF CORRECTION

PATENT NO. : 3,970,617
DATED : July 20, 1976
INVENTOR(S) : Salvatore A. Bruno

It is certified that error appears in the above-identified patent and that said Letters Patent are hereby corrected as shown below:

Claim 1 should read as follows:

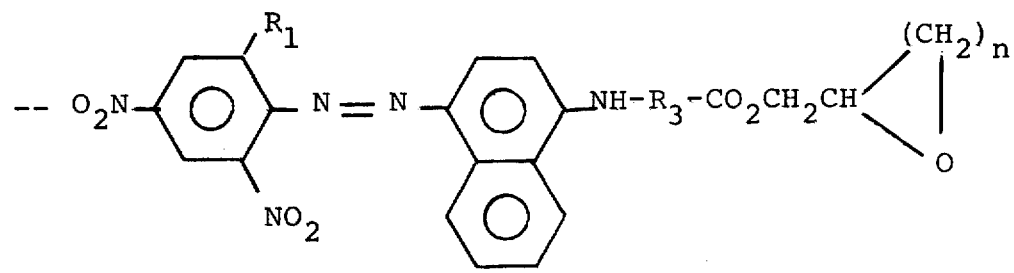

wherein $R_1$ is Br, Cl or CN; $R_3$ is $C_{1-4}$ alkylene; and n is 3 or 4. --

Delete the words "of Claim 1" from Claims 3, 4 and 5.

Signed and Sealed this

Twenty-first Day of September 1976

[SEAL]

Attest:

RUTH C. MASON
Attesting Officer

C. MARSHALL DANN
Commissioner of Patents and Trademarks